(12) United States Patent
O'Brien et al.

(10) Patent No.: US 8,057,999 B2
(45) Date of Patent: *Nov. 15, 2011

(54) EXTRACELLULAR SERINE PROTEASE

(75) Inventors: Timothy J. O'Brien, Little Rock, AR (US); Lowell J. Underwood, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 105 days.

This patent is subject to a terminal disclaimer.

(21) Appl. No.: 12/381,341

(22) Filed: Mar. 11, 2009

(65) Prior Publication Data

US 2010/0120030 A1 May 13, 2010

Related U.S. Application Data

(62) Division of application No. 11/295,040, filed on Dec. 5, 2005, now Pat. No. 7,537,901, which is a division of application No. 08/915,659, filed on Aug. 21, 1997, now Pat. No. 7,014,993.

(51) Int. Cl.
| | | |
|---|---|---|
| C12Q 1/00 | (2006.01) | |
| C12Q 1/68 | (2006.01) | |
| G01N 1/00 | (2006.01) | |
| G01N 21/00 | (2006.01) | |
| G01N 21/75 | (2006.01) | |
| G01N 33/48 | (2006.01) | |
| G01N 33/567 | (2006.01) | |
| G01N 33/574 | (2006.01) | |

(52) U.S. Cl. ............ 435/6; 435/4; 435/7.21; 435/7.23; 436/63; 436/64; 436/164; 436/166; 436/174

(58) Field of Classification Search ................ None
See application file for complete search history.

(56) References Cited

U.S. PATENT DOCUMENTS

| | | | | |
|---|---|---|---|---|
| 5,821,328 | A * | 10/1998 | King et al. | ............ 530/300 |
| 7,067,250 | B1 * | 6/2006 | Underwood et al. | ............ 435/6 |
| 2002/0156006 | A1 * | 10/2002 | Ashkenazi et al. | ............ 514/12 |

* cited by examiner

*Primary Examiner* — Alana M Harris
(74) *Attorney, Agent, or Firm* — Benjamin Aaron Adler

(57) ABSTRACT

The present invention provides a DNA encoding a TADG-14 protein selected from the group consisting of: (a) isolated DNA which encodes a TADG-14 protein; (b) isolated DNA which hybridizes to isolated DNA of (a) above and which encodes a TADG-14 protein; and (c) isolated DNA differing from the isolated DNAs of (a) and (b) above in codon sequence due to the degeneracy of the genetic code, and which encodes a TADG-14 protein. Also provided is a vector capable of expressing the DNA of the present invention adapted for expression in a recombinant cell and regulatory elements necessary for expression of the DNA in the cell.

10 Claims, 9 Drawing Sheets

```
            PRIMER
201
Prom    WVLTAAHC KK    PNLQV....F    LGKHNLRQRE    SSQEQSSVVR    250 AVIHPDY...
Tadg14  WVVTAAHC KK    PKYTV....R    LGDHSLQNKD    GPEQEIPVVQ        SIPHPCY...
Try1    WVVSAGHC YK    SRIQV....R    LGEHNIEVLE    GNEQFINAAK        IIRHPQY...
Scce    WVLTAAHC KM    NEYTV....H    LGSDTLGDRR    A..QRIKASK        SFRHPGY...
Heps    WVLTAAHC FP    ERNRVLSRWR    VFAGAVAQAS    PHGLGLGVQA        VVYHGGYLFF 251
Prom    ...DAASHDQ    DIMLL RLARP    AKLSELIQPL    PLERDCSA..    300 NTTSCHILGW
Tadg14  NSSDVEDHNH    DLMLL QLRDQ    ASLGSKVKPI    SLADHCTQ...       PGQNCTVSGW
Try1    ...DRKTLNN    DIMLI KLSSR    AVINARVSTI    SLPTAPPA...       TGTKCLISGW
Scce    ST...QTHVN    DLMLV KLNSQ    ARLSSMVKKV    RLPSRCEP...       PGTTCTVSGW
Heps    RDPNSEENSN    DIALV HLSSP    LPLTEYIQPV    CLPAAGQALV        DGKICTVTGW 301
Prom    GKTAD..GDF    PDTIQCAYIH    LVSREECEHA    ..TPGQITQN    350 MLCAGDEKYG
Tadg14  GTVTSPRENF    PDTLNCAEVK    IFPQKKCEDA    ..YPGQITDG        MVCAGSSK.G
Try1    GNTASSGADY    PDELQCLDAP    VLSQAKCEAS    ..YPGKITSN        MFCVGFLEGG
Scce    GTTTSPDVTF    PSDLMCVDVK    LISPQDCTKV    ..YKDLLENS        MLCAGIPDSK
Heps    GNTQYYGQQ.    AGVLQEARVP    IISNDVCNGA    DFYGNQIKPK        MFCAGYPEGG
        PRIMER 351
Prom    KDSCQ GDSGG    SEQ ID No. 1
Tadg14  ADTCQ GDSGG    SEQ ID No. 2
Try1    KDSCQ GDSGG    SEQ ID No. 3
Scce    KNACN GDSGG    SEQ ID No. 4
Heps    IDACQ GDSGG    SEQ ID No. 5
        PRIMER
```

```
Neur   477 AGAGGCCACCATGGGACGCCCCCACCCTGTGCAATCCAGCCGTGGATCC 505
T14    506 AGACCTCACCATGGGACGCCCCCGACCTCGTGCGGCCAAGACGTGGATGT 555

527 TTCTGCTTCTGTTCATGGGAGCGTGGGCAGGGCTCACCAGAGCTCAGGGC 576
       556 TCCTGCTCTTGCTGGGGGGAGCCTGGGCAGGACACTCCAGGGCACAGGAG 605

577 TCCAAGATCCTGGAAGGTCGAGAGTGTATACCCCACTCCCAGCCTTGGCA 626
       606 GACAAGGTGCTGGGGGGTCATGAGTGCCAACCCCATTCGCAGCCTTGGCA 655

627 GGCAGCCTTGTTCCAGGGCGAGAGACTGATCTGTGGGGTGTCCTGGTTG 676
       656 GGCGGCCTTGTTCCAGGGCCAGCAACTACTCTGTGGCGGTGTCCTTGTAG 705

677 GAGACAGATGGGTCCTCACGGCAGCCCACTGCAAAAAACAGAAGTACTCC 726
       706 GTGGCAACTGGGTCCTTACAGCTGCCCACTGTAAAAAACCGAAATACACA 755

727 GTGCGTCTGGGTGATCATAGCCTCCAGAGCAGAGATCAGCCGGAGCAGGA 776
       756 GTACGCCTGGGAGACCACAGCCTACAGAATAAAGATGGCCCAGAGCAAGA 805

777 GATCCAGGTGGCTCAGTCTATCCAGCATCCTTGCTACAACAACAGCAACC 826
       806 AATACCTGTGGTTCAGTCCATCCCACACCCCTGCTACAACAGCAGCGATG 855

827 CAGAAGATCACAGTCACGATATAATGCTCATTCGACTGCAGAACTCAGCA 876
       856 TGGAGGACCACAACCATGATCTGATGCTTCTTCAACTGCGTGACCAGGCA 905

877 AACCTCGGGGACAAGGTGAAGCCGGTCCAACTGGCCAATCTGTGTCCCAA 926
       906 TCCCTGGGGTCCAAAGTGAAGCCCATCAGCCTGGCAGATCATTGCACCCA 955

927 AGTTGGCCAGAAGTGCATCATATCAGGCTGGGGCACTGTCACCAGCCCTC 976
       956 GCCTGGCCAGAAGTGCACCGTCTCAGGCTGGGGCACTGTCACCAGTCCCC 1005

977 AAGAGAACTTTCCAAACACCCTCAACTGTGCGGAAGTGAAAATCTATTCC 1026
      1006 GAGAGAATTTTCCTGACACTCTCAACTGTGCAGAAGTAAAAATCTTTCCC 1055
```

Fig. 7A

```
1027 CAGAACAAGTGTGAGACAGCCTATCCAGGGAAGATCACCGAGGGCATGGT 1076
     |||||  |||||||||   ||  || || ||| |||||||  || |||||||||
1056 CAGAAGAAGTGTGAGGATGCTTACCCGGGGCAGATCACAGATGGCATGGT 1105

1077 CTGTGCTGGCAGCAGCAATGGAGCTGACACGTGCCAGGGTGACTCAGGAG 1126
     ||||||  ||||||||||  ||  ||||||||||||||||  ||  ||||
1106 CTGTGCAGGCAGCAGCAAAGGGGCTGACACGTGCCAGGGCGATTCTGGAG 1155

1127 GCCCTCTGGTGTGCGACGGGATGCTCCAGGGCATCACCTCATGGGGCTCA 1176
     ||||  ||||||||  ||  ||||||||||||||||||  ||||||||||
1156 GCCCCGTGGTGTGTGATGGTGCACTCCAGGGCATCACATCCTGGGGCTCA 1205

1177 GACCCTGTGGGAAACCCGAGAAACCTGGAGTCTACACCAAAATCTGCCG 1226
     |||||||||||||  ||||  |||||||| || |||||  ||||||||||
1206 GACCCTGTGGGAGGTCCGACAAACCTGGCGTCTATACCAACATCTGCCG 1255

1227 CTACACTACCTGGATCAAGAAGACCATGGACAACAGGGACTGATCCTGG 1275
     |||||  |||||||||||||||| ||| ||  || || |||||| || |
1256 CTACCTGGACTGGATCAAGAAGATCATAGGCAGCAAGGGCTGATTCTAG 1304
```

Neur  SEQ ID NO: 8
T14   SEQ ID NO: 9

Fig. 7B

```
Tadg14   1 MGRPRPRAAKTWMFLLLLGGAWAGHSRAQEDKVLGGHECQPHSQPWQAAL  50
           ||||  |   |   |||  |||||  ||   |  | || ||||||||||
Neur     1 MGRPPPCAIQPWILLLLFMGAWAGLTRAQGSKILEGRECIPHSQPWQAAL  50

51 FQGQQLLCGGVLVGGNWVLTAAHCKKPKYTVRLGDHSLQNKDGPEQEIPV 100
           |||  |||||||||| ||||||||||  || ||||||||| | |||||| |
        51 FQGERLICGGVLVGDRWVLTAAHCKKQKYSVRLGDHSLQSRDQPEQEIQV 100

101 VQSIPHPCYNSSDVEDHNHDLMLLQLRDQASLGSKVKPISLADHCTQPGQ 150
           ||| ||||||| | ||| || |   |  | ||| |||| |  | ||
       101 AQSIQHPCYNNSNPEDHSHDIMLIRLQNSANLGDKVKPVQLANLCPKVGQ 150

151 KCTVSGWGTVTSPRENFPDTLNCAEVKIFPQKKCEDAYPGQITDGMVCAG 200
           ||  |||||||||| |||| |||||||| | ||| |||| || ||||||
       151 KCIISGWGTVTSPQENFPNTLNCAEVKIYSQNKCERAYPGKITEGMVCAG 200

201 SSKGADTCQGDSGGPLVCDGALQGITSWGSDPCGRSDKPGVYTNICRYLD 205
           || |||||||||||||||| ||||||||||||| |  ||||||| ||||
       201 SSNGADTCQGDSGGPLVCDGMLQGITSWGSDPCGKPEKPGVYTKICRYTT 250

251 WIKKIIGSKG  260       SEQ ID NO: 7
           ||||
       251 WIKKTMDNRD  260       SEQ ID NO: 8
```

Fig. 8

EXTRACELLULAR SERINE PROTEASE

CROSS-REFERENCE TO RELATED APPLICATIONS

This is a divisional application of U.S. Ser. No. 11/295,040, filed Dec. 5, 2005, now U.S. Pat. No. 7,537,901, which is a divisional of non-provisional application U.S. Ser. No. 08/915,659, filed Aug. 21, 1997, now U.S. Pat. No. 7,014,993.

BACKGROUND OF THE INVENTION

1. Field of the Invention

The present invention relates generally to the fields of cellular biology and the diagnosis of neoplastic disease. More specifically, this invention relates to a novel extracellular serine protease termed Tumor Antigen Derived Gene-14 (TADG-14).

2. Description of the Related Art

Extracellular proteases have been directly associated with tumor growth, shedding of tumor cells and invasion of target organs. Individual classes of proteases are involved in, but not limited to (1) the digestion of stroma surrounding the initial tumor area, (2) the digestion of the cellular adhesion molecules to allow dissociation of tumor cells; and (3) the invasion of the basement membrane for metastatic growth and the activation of both tumor growth factors and angiogenic factors.

The prior art is deficient in the lack of effective means of screening to identify proteases overexpressed in carcinoma. The present invention fulfills this longstanding need in the art.

SUMMARY OF THE INVENTION

The present invention discloses a screening system to identify proteases overexpressed in carcinoma by examining PCR products amplified from early-stage tumors, metastatic tumors, and normal ovarian epithelium.

In one embodiment of the present invention, there is provided a DNA encoding a TADG-14 protein selected from the group consisting of: (a) isolated DNA which encodes a TADG-14 protein; (b) isolated DNA which hybridizes to isolated DNA of (a) above and which encodes a TADG-14 protein; and (c) isolated DNA differing from the isolated DNAs of (a) and (b) above in codon sequence due to the degeneracy of the genetic code, and which encodes a TADG-14 protein.

In another embodiment of the present invention, there is provided a vector capable of expressing the DNA of the present invention adapted for expression in a recombinant cell and regulatory elements necessary for expression of the DNA in the cell.

In yet another embodiment of the present invention, there is provided a host cell transfected with the vector of the present invention where the vector expresses a TADG-14 protein.

In still another embodiment of the present invention, there is provided a method of detecting expression of a TADG-14 mRNA, comprising the steps of: (a) contacting mRNA obtained from the cell with the labeled hybridization probe; and (b) detecting hybridization of the probe with the mRNA.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows a comparison of the amino acid sequence of TADG-14's catalytic domains.

FIG. 6 shows the complete sequence of the TADG-14 transcript including the open reading frame and common domains.

FIGS. 7A-7B show the homology of TADG-14 with mouse neuropsin. There was approximately 76% identity for the open reading frame and low homology outside of the open reading frame.

FIG. 8 shows the amino acid homology of TADG-14 with mouse neuropsin.

DETAILED DESCRIPTION OF THE INVENTION

Figure 1:
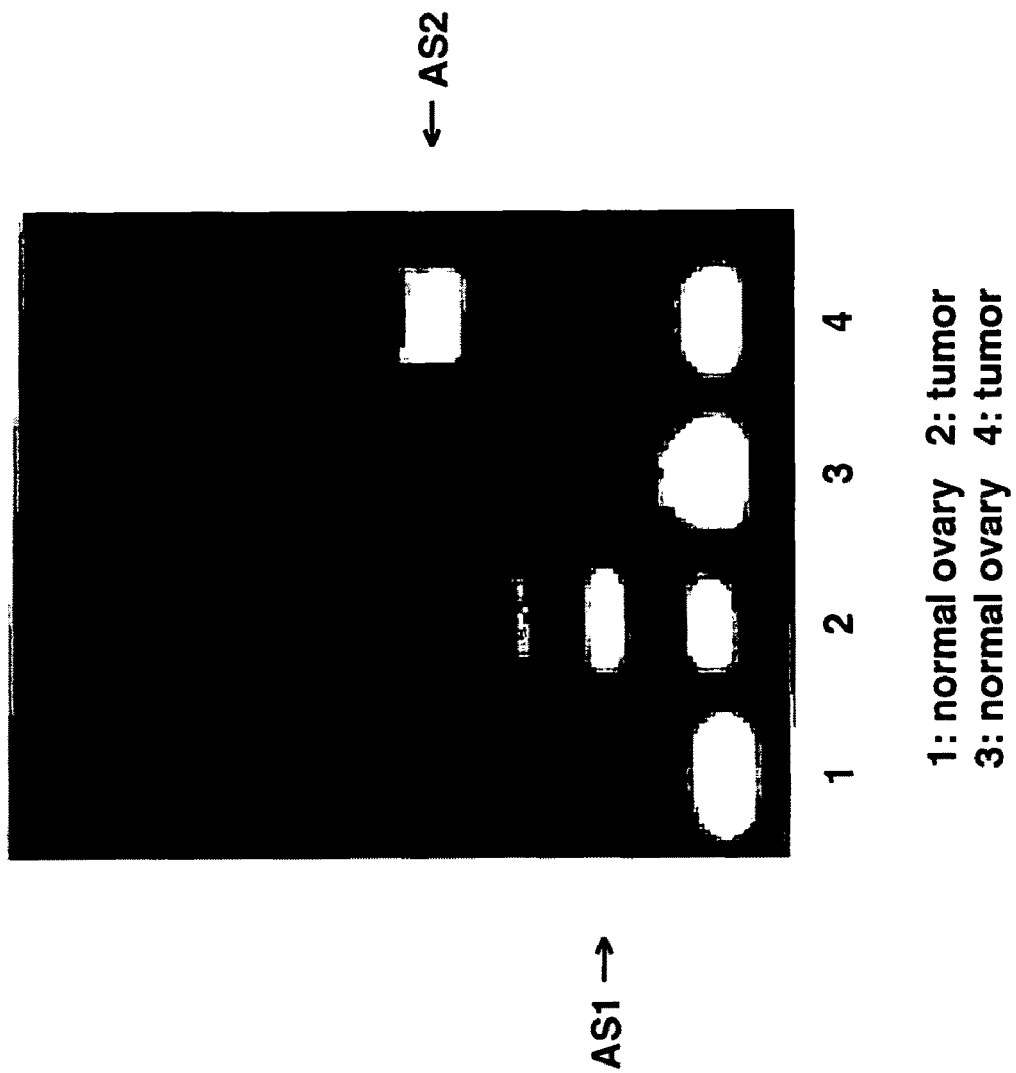
FIG. 1 shows a comparison of PCR products derived from normal and carcinoma cDNA as shown by staining in an agarose gel. Two distinct bands (lane 2) were present in the primer pair sense-His-antisense Asp (AS1) and multiple bands of about 500 base pairs are noted in the carcinoma lane for the sense-His antisense-Ser (AS2) primer pairs (lane 4).

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The TADG-14 cDNA is 1343 base pairs long (SEQ ID NO: 6) and encoding for a 260 amino acid protein (SEQ ID NO: 7). The availability of the TADG-14 gene opens the way for a number of studies that can lead to various applications. For example, if the TADG-14 gene underlies a specific human genetic disease, the cDNA can be the basis for a diagnostic predictive test.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed.

(1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The amino acids described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. Abbreviations for amino acids may be used in keeping with standard polypeptide nomenclature, J. Biol. Chem., 243:3552-59 (1969) as shown in the following Table of Correspondence.

TABLE OF CORRESPONDENCE

| 1 Letter Symbol | 3-Letter Abbreviation | Amino Acid Name |
| --- | --- | --- |
| A | Ala | alanine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagines |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element, e.g., plasmid, chromosome, or virus, that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides, adenine, guanine, thymine, or cytosine, in its either single-stranded form, or a double-stranded helix. This term refers only to the primary and secondary structure of the molecule and does not limit it to any particular tertiary forms. Thus, this term includes double-stranded DNA found, inter alia, in linear DNA molecules, e.g., restriction fragments, viruses, plasmids, and chromosomes. The structures herein are discussed according to the normal convention of giving only the sequence in the 5' to 3' direction along the nontranscribed strand of DNA, i.e., the strand having a sequence homologous to the mRNA.

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' amino terminus and a translation stop codon at the 3' carboxyl terminus. A coding sequence can include, but is not limited to, prokaryotic sequences, cDNA from eukaryotic mRNA, genomic DNA sequences from eukaryotic, e.g., mammalian, DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream, i.e., 3' direction, coding sequence. For purposes of defining the present invention, the promoter sequence is bounded at its 3' terminus by the transcription initiation site and extends upstream, i.e., 5' direction, to include the minimum number of bases or elements necessary to initiate transcription at levels detectable above background. Within the promoter sequence will be found a transcription initiation site, as well as protein binding domains or consensus sequences responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide N-terminal to the polypeptide that communicates to the host cell to direct the polypeptide to the cell surface or secrete the polypeptide into the media. This signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprising two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75%, preferably at least about 80% and most preferably at least about 90% or 95%, of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature, e.g., a cDNA where the genomic coding sequence contains introns, or synthetic sequences having codons different than the native gene. Allelic variations or naturally occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, b-glucuronidase, b-D-glucosidase, b-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantity of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a human TADG-14 protein of the present invention can be used to transform a host using any of the techniques commonly known to those of ordinary skill in the art. Especially preferred is the use of a vector containing coding sequences for the gene which encodes a human TADG-14 protein of the present invention for purposes of prokaryote transformation.

Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The invention includes a substantially pure DNA encoding a TADG-14 protein, a strand of which DNA will hybridize at high stringency to a probe containing a sequence of at least 15 consecutive nucleotides of SEQ ID NO: 6. The protein encoded by the DNA of this invention may share at least 80% sequence identity, preferably 85%, more preferably 90%, and most preferably 95%, with the amino acids listed in FIG. 6 for SEQ ID NO: 7. More preferably, the DNA includes the coding sequence of the nucleotides of FIG. 6 in SEQ ID NO:6, or a degenerate variant of such a sequence.

Figure 6:
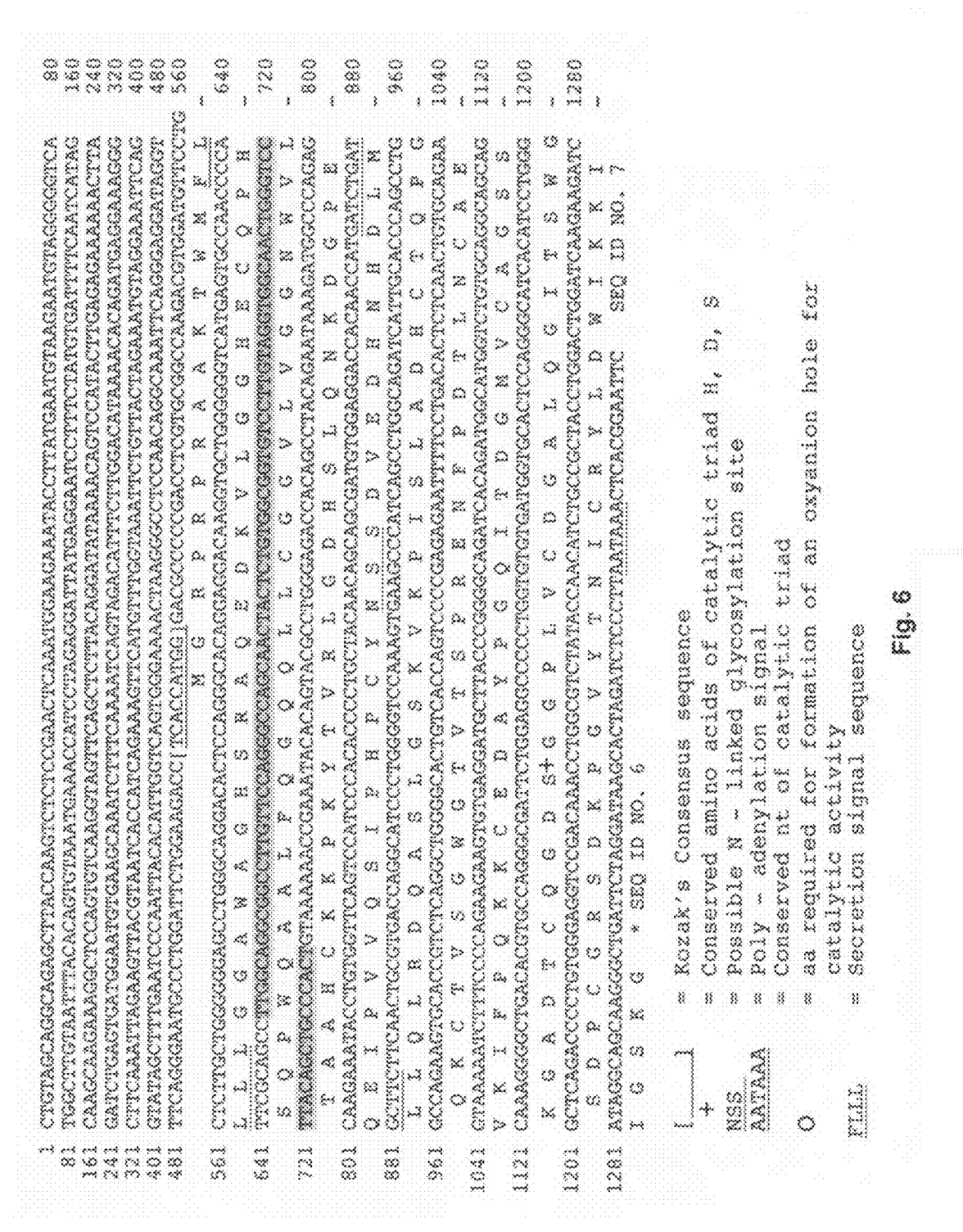

The probe to which the DNA of the invention hybridizes preferably consists of a sequence of at least 20 consecutive nucleotides, more preferably 40 nucleotides, even more preferably 50 nucleotides, and most preferably 100 nucleotides or more up to 100% of the coding sequence of the nucleotides listed in FIG. 6 in SEQ ID NO: 6 or the complement thereof. Such a probe is useful for detecting expression of TADG-14 in a human cell by a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides, preferably 20, more preferably 30, even more preferably 50, and, most preferably all, of the region from nucleotides 1 to 1343 of the nucleotides listed in FIG. 6 in SEQ ID NO: 6.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation, i.e., partial or total purification, of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule, e.g., a cDNA or a genomic or cDNA fragment produced by polymerase chain reaction (PCR) or restriction endonuclease digestion, independent of other sequences. It also includes a recombinant DNA which is part of a hybrid gene encoding additional polypeptide sequence, e.g., a fusion protein. Also included is a recombinant DNA which includes a portion of the nucleotides listed in FIG. 6 in SEQ ID NO: 6 which encodes an alternative splice variant of TADG-14.

The DNA may have at least about 70% sequence identity to the coding sequence of the nucleotides listed in FIG. 6 in SEQ ID NO: 6, preferably at least 75%, e.g. at least 80%, and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10 nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software, e.g., Sequence Analysis Software Package of the Genetics Computer Group, University of Wisconsin Biotechnology Center, 1710 University Avenue, Madison, Wis. 53705.

The present invention comprises a vector comprising a DNA sequence coding for a which encodes a human TADG-14 protein and the vector is capable of replication in a host which comprises, in operable linkage: a) an origin of replication; b) a promoter; and c) a DNA sequence coding for the protein. Preferably, the vector of the present invention contains a portion of the DNA sequence shown in SEQ ID NO: 6. A "vector" may be defined as a replicable nucleic acid construct, e.g., a plasmid or viral nucleic acid. Vectors may be used to amplify and/or express nucleic acid encoding TADG-14 protein. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation.

Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein which has been separated from at least some of those components which naturally accompany it. Typically, the protein is substantially pure when it is at least 60%, by weight, free from the proteins and other naturally occurring organic molecules with which it is naturally associated in vivo. Preferably, the purity of the preparation is at least 75%, more preferably at least 90%, and most preferably at least 99%, by weight. A substantially pure TADG-14 protein may be obtained, for example, by extraction from a natural source; by expression of a recombinant nucleic acid encoding an TADG-14 polypeptide or by chemically synthesizing the protein. Purity can be measured by any appropriate method, e.g., column chromatography, such as immunoaffinity chromatography, using an antibody specific for TADG-14, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in E. coli, other prokaryotes, or any other organism in which they do not naturally occur.

In addition to substantially full-length proteins, the invention also includes fragments, e.g., antigenic fragments, of the TADG-14 protein in SEQ ID NO: 7. As used herein, "fragment," as applied to a polypeptide, will ordinarily be at least 10 residues, more typically at least 20 residues, and preferably at least 30, e.g., 50, residues in length, but less than the entire, intact sequence. Fragments of the TADG-14 protein can be generated by methods known to those skilled in the art, e.g., by enzymatic digestion of naturally occurring or recombinant TADG-14 protein, by recombinant DNA techniques using an expression vector that encodes a defined fragment of TADG-14, or by chemical synthesis. The ability of a candidate fragment to exhibit a characteristic of TADG-14, e.g., binding to an antibody specific for TADG-14, can be assessed by methods described herein. Purified TADG-14 or antigenic fragments of TADG-14 can be used to generate new antibodies or to test existing antibodies, e.g., as positive controls in a diagnostic assay, by employing standard protocols known to those skilled in the art. Included in this invention are polyclonal antisera generated by using TADG-14 or a fragment of TADG-14 as the immunogen in, e.g., rabbits. Standard protocols for monoclonal and polyclonal antibody production known to those skilled in this art are employed. The monoclonal antibodies generated by this procedure can be screened for the ability to identify recombinant TADG-14 cDNA clones, and to distinguish them from known cDNA clones.

Further included in this invention are TADG-14 proteins which are encoded at least in part by portions of SEQ ID NO: 7, e.g., products of alternative mRNA splicing or alternative protein processing events, or in which a section of TADG-14 sequence has been deleted. The fragment, or the intact TADG-14 polypeptide, may be covalently linked to another polypeptide, e.g. which acts as a label, a ligand or a means to increase antigenicity.

The invention also includes a polyclonal or monoclonal antibody which specifically binds to TADG-14. The invention encompasses not only an intact monoclonal antibody, but also an immunologically-active antibody fragment, e.g., a Fab or (Fab)$_2$ fragment, an engineered single chain Fv molecule or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g. a radioactive label, non-radioactive isotopic label, fluorescent label, chemiluminescent label, paramagnetic label, enzyme label, or colorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3$H, $^{125}$I, $^{131}$I, $^{32}$P, $^{35}$S, $^{14}$C, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) JACC 14, 472-480; Shreve et al., (1986) Magn. Reson. Med. 3, 336-340; Wolf, G. L., (1984) Physiol. Chem. Phys. Med. NMR 16, 93-95; Wesbey et al., (1984) Physiol. Chem. Phys. Med. NMR 16, 145-155; Runge et al., (1984) Invest. Radiol. 19, 408-415. Examples of suitable fluorescent labels include a fluorescein label, an isothiocyanate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) Clin. Chim. Acta 70, 1-31; and Schurs et al., (1977) Clin. Chim. Acta 81, 1-40. Coupling techniques mentioned in the latter are the glutaraldehyde method, the periodate method, the dimaleimide method, the m-maleimidobenzyl-N-hydroxysuccinimide ester method.

Also within the invention is a method of detecting TADG-14 protein in a biological sample, which includes the steps of contacting the sample with the labeled antibody, e.g., radioactively tagged antibody specific for TADG-14, and determining whether the antibody binds to a component of the sample.

As described herein, the invention provides a number of diagnostic advantages and uses. For example, the TADG-14 protein is useful in diagnosing cancer in different tissues since this protein is absent in highly proliferating cells. Antibodies or antigen-binding fragments thereof which bind to an epitope specific for TADG-14 are useful in a method of detecting TADG-14 protein in a biological sample for diagnosis of cancerous or neoplastic transformation. This method includes the steps of obtaining a biological sample, e.g., cells, blood, tissue, etc., from a patient suspected of having cancer, contacting the sample with a labelled antibody, e.g., radioactively tagged antibody, specific for TADG-14 and detecting the TADG-14 protein using standard immunoassay techniques such as an ELISA. Antibody binding to the biological sample indicates that the sample contains a component which specifically binds to an epitope within TADG-14.

Likewise, a standard Northern blot assay can be used to ascertain the relative amounts of TADG-14 mRNA in a cell or tissue obtained from a patient suspected of having cancer, in accordance with conventional Northern hybridization techniques known to those persons of ordinary skill in the art. This Northern assay uses a hybridization probe, e.g. radiolabeled TADG-14 cDNA, either containing the full-length, single stranded DNA having a sequence complementary to SEQ ID NO: 6 (FIG. 6), or a fragment of that DNA sequence at least 20, preferably at least 30, more preferably at least 50, and most preferably at least 100 consecutive nucleotides in length. The DNA hybridization probe can be labeled by any of the many different methods known to those skilled in this art.

Antibodies to the TADG-14 protein can be used in an immunoassay to detect increased levels of TADG-14 protein expression in tissues suspected of neoplastic transformation. These same uses can be achieved with Northern blot assays and analyses.

The present invention is directed to DNA encoding a TADG-14 protein selected from the group consisting of: (a) isolated DNA which encodes a TADG-14 protein; (b) isolated DNA which hybridizes to isolated DNA of (a) above and which encodes a TADG-14 protein; and (c) isolated DNA differing from the isolated DNAs of (a) and (b) above in codon sequence due to the degeneracy of the genetic code, and which encodes a TADG-14 protein. Preferably, the DNA has the sequence shown in SEQ ID NO. 6. More preferably, the DNA encodes a TADG-14 protein having the amino acid sequence shown in SEQ ID NO. 7.

The present invention is also directed to a vector capable of expressing the DNA of the present invention adapted for expression in a recombinant cell and regulatory elements necessary for expression of the DNA in the cell. Preferably, the vector contains DNA encoding a TADG-14 protein having the amino acid sequence shown in SEQ ID NO. 7.

The present invention is also directed to a host cell transfected with the vector described herein where the vector expresses a TADG-14 protein. Representative host cells include bacterial cells, mammalian cells and insect cells.

The present invention is also directed to a isolated and purified TADG-14 protein coded for by DNA selected from the group consisting of: (a) isolated DNA which encodes a TADG-14 protein; (b) isolated DNA which hybridizes to isolated DNA of (a) above and which encodes a TADG-14 protein; and (c) isolated DNA differing from the isolated DNAs of (a) and (b) above in codon sequence due to the degeneracy of the genetic code, and which encodes a TADG-14 protein. Preferably, the isolated and purified TADG-14 protein has the amino acid sequence shown in SEQ ID NO. 7.

The present invention is also directed to a method of detecting expression of the protein described herein, comprising the steps of: (a) contacting mRNA obtained from the cell with the labeled hybridization probe; and (b) detecting hybridization of the probe with the mRNA.

The following examples are given for the purpose of illustrating various embodiments of the invention and are not meant to limit the present invention in any fashion.

Example 1

Tissue Collection and Storage

Upon patient hysterectomy, bilateral salpingo-oophorectomy, or surgical removal of neoplastic tissue, the specimen is retrieved and placed on ice. The specimen was then taken to the resident pathologist for isolation and identification of specific tissue samples. Finally, the sample was frozen in liquid nitrogen, logged into the laboratory record and stored at −80° C. Additional specimens were frequently obtained from the Cooperative Human Tissue Network (CHTN). These samples were prepared by the CHTN and shipped to us on dry ice. Upon arrival, these specimens were logged into the laboratory record and stored at −80° C.

Example 2 mRNA Isolation and cDNA Synthesis

Messenger RNA (mRNA) isolation was performed according to the manufacturer's instructions using the Mini RiboSep™ Ultra mRNA isolation kit purchased from Becton Dickinson (Cat. NO. 30034). This was an oligo(dt) chromatography based system of mRNA isolation. The amount of mRNA recovered was quantitated by UV spectrophotometry.

First strand complementary DNA (cDNA) was synthesized using 5.0 mg of mRNA and either random hexamer or oligo (dT) primers according to the manufacturer's protocol utilizing a first strand synthesis kit obtained from Clontech (Cat. NO. K1402-1). The purity of the cDNA was evaluated by PCR using primers specific for the p53 gene. These primers span an intron such that pure cDNA can be distinguished from cDNA that is contaminated with genomic DNA.

Example 3

PCR Reactions

Reactions were carried out as follows: first strand cDNA generated from 50 ng of mRNA will be used as template in the presence of 1.0 mM MgCl2, 0.2 mM dNTPs, 0.025 U Taq polymerase/ml of reaction, and 1× buffer supplied with enzyme. In addition, primers must be added to the PCR reaction. Degenerate primers that may amplify a variety of cDNAs are used at a final concentration of 2.0 mM each, whereas primers which amplify specific cDNAs are added to a final concentration of 0.2 mM each.

After initial denaturation at 95° C. for 3 minutes, thirty cycles of PCR are carried out in a Perkin Elmer Gene Amp 2400 thermal cycler. Each cycle consists of 30 seconds of denaturation at 95° C., 30 seconds of primer annealing at the appropriate annealing temperature*, and 30 seconds of extension at 72° C. The final cycle will be extended at 72° C. for 7 minutes. To ensure that the reaction succeeded, a fraction of the mixture will be electrophoresed through a 2% agarose/TAE gel stained with ethidium bromide (final concentration 1 mg/ml). The annealing temperature varies according to the primers that are used in the PCR reaction. For the reactions involving degenerate primers, an annealing temperature of 48° C. were used. The appropriate annealing temperature for the TADG-14 and β-tubulin specific primers is 62° C.

Example 4

T-Vector Ligation and Transformations

The purified PCR products are ligated into the Promega T-vector plasmid and the ligation products are used to transform JM109 competent cells according to the manufacturer's instructions (Promega Cat. NO.A3610). Positive colonies were cultured for amplification, the plasmid DNA isolated by means of the Wizard™ Minipreps DNA purification system (Promega cat #A7500), and the plasmids were digested with ApaI and SacI restriction enzymes to determine the size of the insert. Plasmids with inserts of the size(s) visualized by the previously described PCR product gel electrophoresis were sequenced.

Example 5

DNA Sequencing

Utilizing a plasmid specific primer near the cloning site, sequencing reactions were carried out using PRISM™ Ready Reaction Dye Deoxy™ terminators (Applied Biosystems Cat. NO. 401384) according to the manufacturer's instructions. Residual dye terminators were removed from the completed sequencing reaction using a Centri-sep™ spin column (Princeton Separation Cat. NO. CS-901). An Applied Biosystems Model 373A DNA Sequencing System was available and was used for sequence analysis. Based upon the determined sequence, primers that specifically amplify the gene of interest were designed and synthesized.

Example 6

Northern Blot Analysis mRNAs (approximately 5 mg) were size separated by electrophoresis through a 6.3% formaldehyde, 1.2% agarose gel in 0.02 M MOPS, 0.05 M sodium acetate (pH 7.0), and 0.001 M EDTA. The mRNAs were then blotted to Hybond-N (Amersham) by capillary action in 20×SSPE. The RNAs are fixed to the membrane by baking for 2 hours at 80° C. Additional multiple tissue northern (MTN) blots were purchased from CLONTECH Laboratories, Inc. These blots include the Human MTN blot (Cat. NO. 7760-1), the Human MTN II blot (Cat. NO. 7759-1), the Human Fetal MTN II blot (Cat. No. 7756-1), and the Human Brain MTN III blot (Cat. NO. 7750-1). The appropriate probes were radiolabeled utilizing the Prime-a-Gene Labelling System available from Promega (cat#U1100). The blots were probed and stripped according to the ExpressHyb Hybridization Solution protocol available from CLONTECH (Cat. Nos. 8015-1 or 8015-2).

Example 7

Quantitative PCR

Quantitative-PCR was performed in a reaction mixture consisting of cDNA derived from 50 ng of mRNA, 5 pmol of sense and antisense primers for TADG-14 and the internal control β-tubulin, 0.2 mmol of dNTPs, 0.5 mCi of [α-$^{32}$P] dCTP, and 0.625 U of Taq polymerase in 1× buffer in a final volume of 25 ml. This mixture was subjected to 1 minute of denaturation at 95° C. followed by 30 cycles of denaturation for 30 seconds at 95° C., 30 seconds of annealing at 62° C., and 1 minute of extension at 72° C. with an additional 7 minutes of extension on the last cycle. The product was electrophoresed through a 2% agarose gel for separation, the gel was dried under vacuum and autoradiographed. The relative radioactivity of each band was determined by PhosphoImager from Molecular Dynamics.

Example 8

Primers

The present invention describes the use of primers directed to conserved areas of the serine protease class to identify members of that class which are overexpressed in carcinoma. Several genes were identified and cloned in other tissues, but not previously associated with ovarian carcinoma. The present invention describes a novel protease identified in ovarian carcinoma. This gene was identified using primers to the conserved area surrounding the catalytic domain amino acid histidine and the catalytic domain amino acid serine which is about 150 amino acids downstream towards the carboxyl end.

The gene encoding the novel extracellular serine protease of the present invention was identified from a group of proteases overexpressed in carcinoma by subcloning and sequencing the appropriate PCR products. An example of such a PCR reaction is given in FIG. 1. Subcloning and sequencing of individual bands from such amplification provided a basis for identifying the novel protease of the present invention.

Example 9

Expression of TADG-14 Protein

The sequence determined for the catalytic domain of TADG-14 is presented in FIG. 2 and is consistent with other serine proteases and specifically contains conserved amino acids appropriate for the catalytic domain of the serine protease family. Specific primers (20 mers) derived from this sequence were used.

Figure 3:
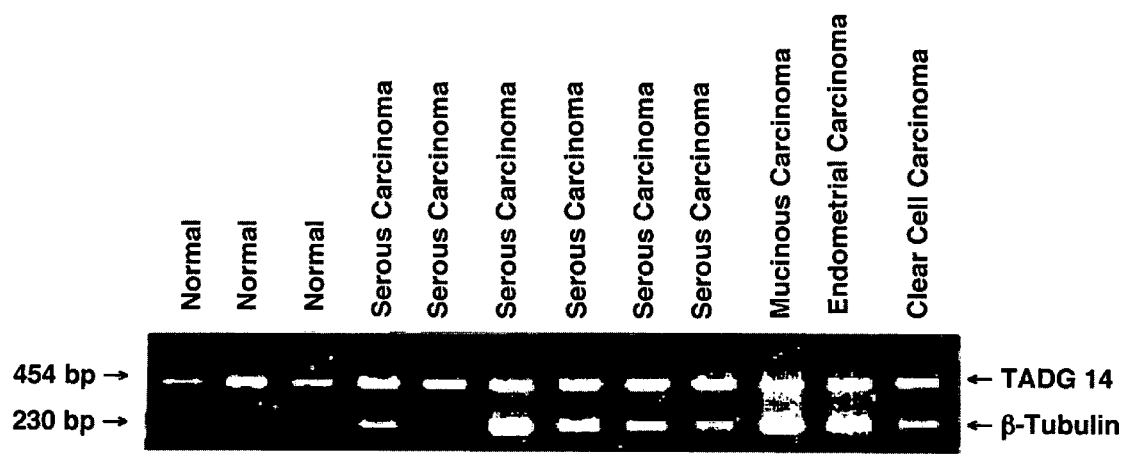
FIG. 3 shows the overexpression of TADG-14 in ovarian carcinomas.
Figure 4:
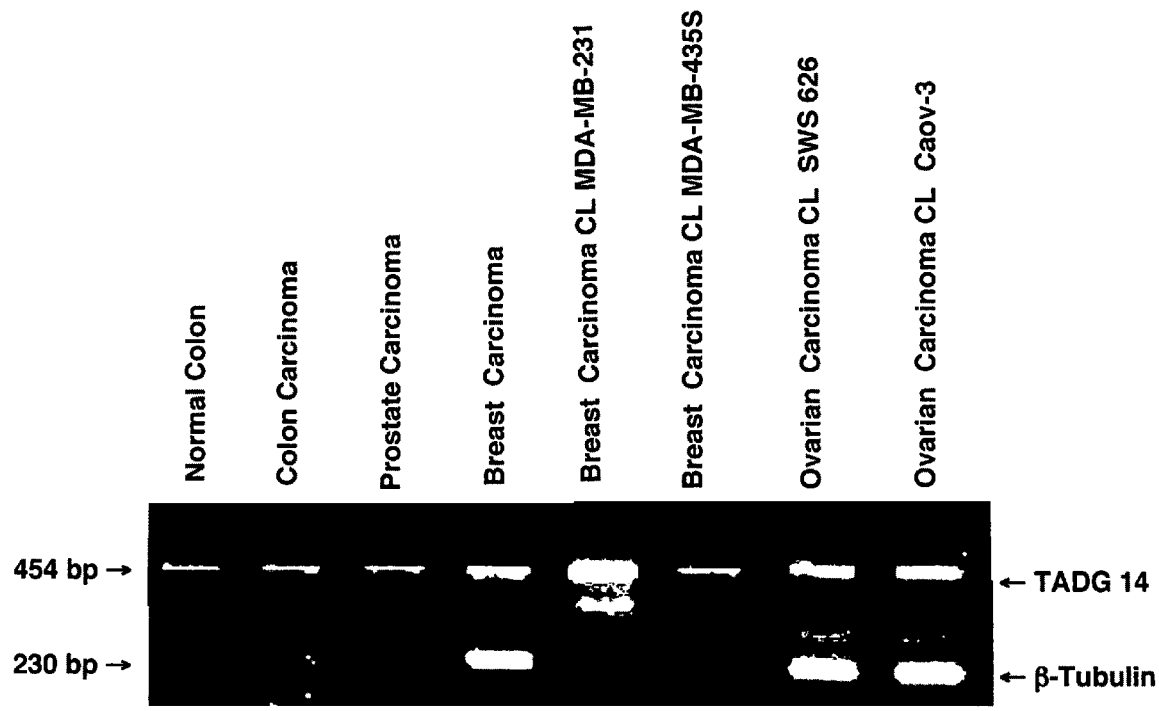
FIG. 4 shows the TADG-14 expression in tumors and cell lines.

A series of normal and tumor cDNAs were examined to determine the expression of the TADG-14 protein. In a series of three normals compared to nine carcinomas using b-tubulin as an internal control for PCR amplification, TADG-14 was significantly overexpressed in eight of the nine carcinomas and either was not detected or was detected at a very low level in normal epithelial tissue (FIG. 3). This evaluation was extended to a standard panel of about 35 tumors. Using these specific primers, the expression of this gene was also examined in both tumor cell lines and other tumor tissues as shown in FIG. 4. The expression of TADG-14 was also observed in breast carcinoma and colon carcinoma. TADG-14 expression was not noted in other tissues. For example, TADG-14 was not present in detectable levels by Northern blot analysis in any of the following normal tissues: fetal lung, fetal heart, fetal brain, fetal kidney, adult spleen, thymus, prostate, testis, ovary, small intestine, colon, peripheral blood leukocytes, heart, placenta, lung, liver, skeletal muscle, kidney, pancreas, amygdala, caudate nucleus, corpus callosum, hippocampus, whole brain, subthalamic nucleus and thalamus.

Figure 5:
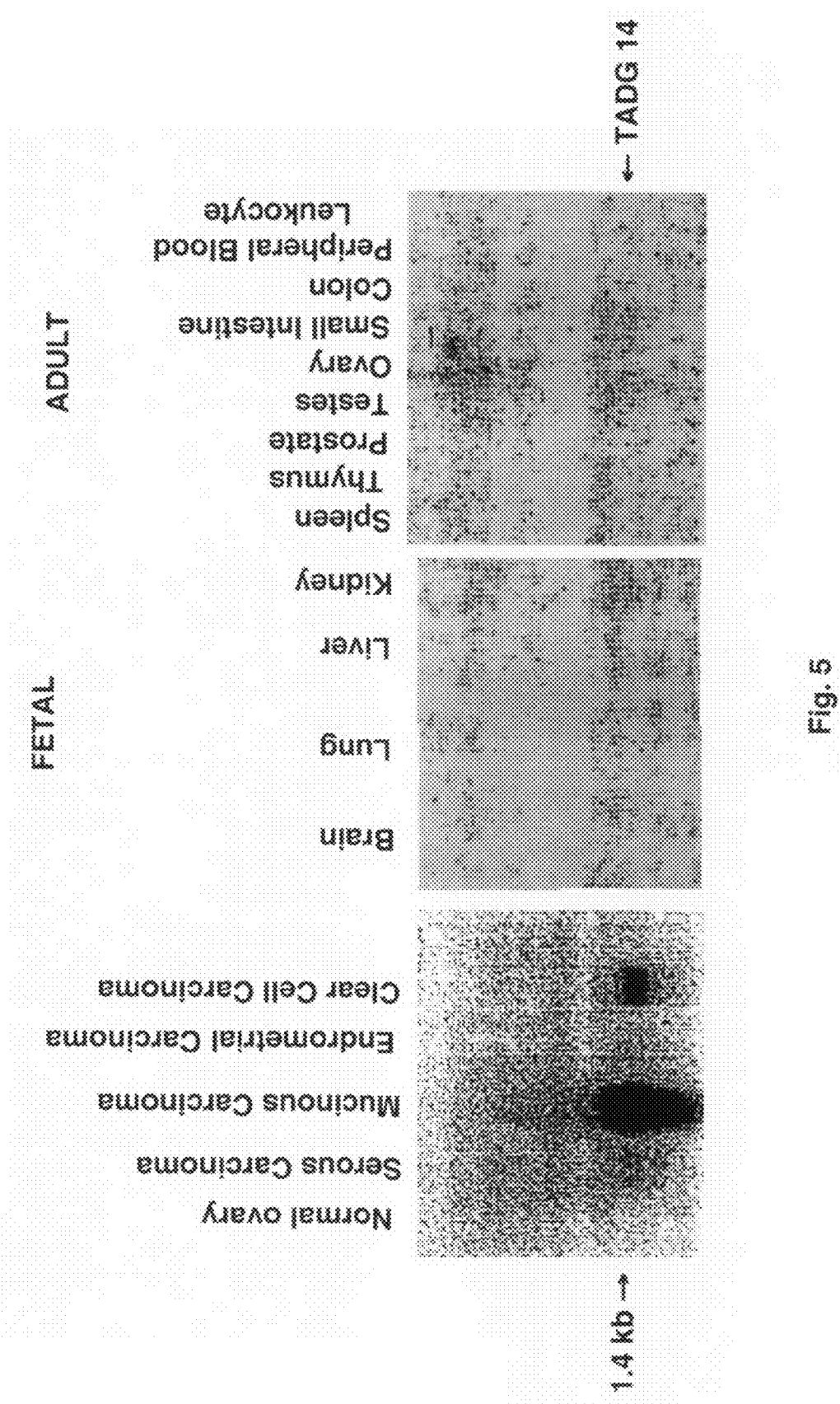
FIG. 5 shows the blots of TADG-14 expression in fetal, adult and ovarian carcinoma tissues.

Using the specific sequence for TADG-14 covering the full domain of the catalytic site as a probe for Northern blot analysis, three Northern blots were examined: one derived from ovarian tissues, both normal and carcinoma; one from fetal tissues; and one from adult normal tissues. As noted in FIG. 5, abundant transcripts for TADG-14 were noted in ovarian carcinomas. Transcripts were noted in all carcinomas, but at lower levels in some sub-types of ovarian cancer. Furthermore, no transcript was observed from normal ovarian tissue. The transcript size was found to be approximately 1.4 kb. Of particular note is the fact that in the fetal tissue examined including brain, lung, liver, kidney and in multiple adult tissues examined, none of these blots showed expression for the TADG-14 transcript. The hybridization for the fetal and adult blots was appropriate and done with the same probe as with the ovarian tissue. Subsequent to this examination, it was confirmed that these blots contained other detectable mRNA transcripts Using the base sequence derived from the original full-length PCR clone corresponding to nucleotides 713-1160 of the catalytic domain as a probe to screen libraries, an ovarian carcinoma library derived from ascites tumor cells was examined for the presence of TADG-14. Four clones were obtained, two of which covered the complete mRNA 1.4 kb transcript of the TADG-14 gene. The complete nucleotide sequence of SEQ ID NO: 6 is provided in FIG. 6 along with translation of the open reading frame as SEQ ID NO: 7.

In the nucleotide sequence, there is a Kozak sequence typical of sequences upstream from the initiation site of translation. There is also a polyadenylation signal sequence and a poly-A tail. The open reading frame consists of a 260 amino acid sequence (SEQ ID NO: 7) which includes a secretion signal sequence in the first 25 amino acids confirming the extracellular processing of the protease. Also a clear delineation of the catalytic domain conserved histidine, aspartic acid, serine series along with a series of amino acids conserved in the serine protease family is indicated.

Examination of the databases for both the expressed tag sequence and complete transcripts provided seven genes that had significant homology to this newly identified serine protease. One gene was identified from mouse brain and a comparison of the nucleotide homology is provided in FIGS. 7A-7B. A comparison of the homology of the amino acid sequence is provided in FIG. 8. Alignment of TADG-14 with mouse neuropsin revealed 77.2% similarity and 72.2% identity at the amino acid levels for these two genes. Given that the size of the mouse transcript is 1.4 kb and that the mouse gene contains 260 amino acids and there is greater than 70% homology, this gene may be a human equivalent of the mouse neuropsin gene or a member of neuropsin-like genes.

TADG-14 is secreted and expressed early in tumor development and has invasive capacity. TADG-14 therefore is a potential diagnostic for ovarian and other cancers. TADG-14 also may be a target for intervention in regulating tumor spread by inhibition, gene therapy, or antibody inactivation technology. In addition to its obvious usefulness in ovarian carcinoma and other carcinomas including the preliminary data on breast and prostate, the neuropsin-like qualities may provide an opportunity for usefulness in neuropathologic disorders.

Any patents or publications mentioned in this specification are indicative of the levels of those skilled in the art to which the invention pertains. These patents and publications are herein incorporated by reference to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for diagnosing cancer in an individual, comprising:
   detecting Tumor Antigen Derived Gene-14 (TADG-14) mRNA encoding a TADG-14 protein of SEQ ID NO: 7 in a biological sample of an individual, wherein the presence of TADG-14 mRNA indicates the individual has a cancer.

2. The method of claim 1, wherein detecting TADG-14 comprises:
   contacting mRNA present within cells or tissue comprising the biological sample with a labeled hybridization probe having a sequence complementary to a DNA encoding TADG-14 protein or a fragment of said DNA; and
   determining if said labeled hybridization probe hybridizes with mRNA via detection of the label.

3. The method of claim 2, wherein said DNA encoding TADG-14 protein has the sequence shown in SEQ ID No. 6.

4. A method for diagnosing cancer in an individual, comprising:
   obtaining a cell or tissue sample from an individual;
   contacting mRNA obtained from the cell sample with a labeled hybridization probe having a sequence complementary to a DNA of SEQ ID NO: 6 encoding TADG-14 protein or a fragment of said DNA; and
   determining if said labeled hybridization probe hybridizes with the mRNA via detection of the label, wherein the hybridization of the labeled probe to the mRNA is indicative of the presence of a cancer in the individual.

5. The method of claim 4, wherein said DNA encodes a TADG-14 protein with the amino acid sequence shown in SEQ ID NO: 7.

6. The method of claim 4, wherein said cancer is ovarian cancer, breast cancer, colon cancer, or prostate cancer.

7. A method for detecting Tumor Antigen Derived Gene-14 (TADG-14) in a biological sample from an individual, comprising:
   isolating mRNA from the sample;
   synthesizing complementary DNA (cDNA) therefrom;
   PCR amplifying the cDNA with primers specific for a TADG-14 DNA of SEQ ID NO: 6 to form an amplified product, thereby detecting the TADG-14 in the sample.

8. The method of claim 7, wherein the biological sample is blood, cells, tissue, or plasma.

9. The method of claim 7, wherein the individual has ovarian cancer, breast cancer, colon cancer, or prostate cancer.

10. The method of claim 1, wherein detecting TADG-14 mRNA comprises PCR, Northern blot or DNA hybridization probes.

* * * * *

SEQUENCE LISTING

```
<160> NUMBER OF SEQ ID NOS: 10

<210> SEQ ID NO 1
<211> LENGTH: 144
<212> TYPE: PRT
<213> ORGANISM: unknown
<220> FEATURE:
<221> NAME/KEY: DOMAIN
<223> OTHER INFORMATION: Amino acid sequence of Protease m (Prom)
      catalytic domain

<400> SEQUENCE: 1

Trp Val Leu Thr Ala Ala His Cys Lys Lys Pro Asn Leu Gln Val
1               5                   10                  15

Phe Leu Glu Lys His Asn Leu Arg Gln Arg Glu Ser Ser Gln Glu
                20                  25                  30

Gln Ser Ser Val Val Arg Ala Val Ile His Pro Asp Tyr Asp Ala
                35                  40                  45

Ala Ser His Asp Gln Asp Ile Met Leu Leu Arg Leu Ala Arg Pro
                50                  55                  60

Ala Lys Leu Ser Glu Leu Ile Gln Pro Leu Pro Leu Glu Arg Asp
                65                  70                  75

Cys Ser Ala Asn Thr Thr Ser Cys His Ile Leu Gly Trp Gly Lys
                80                  85                  90

Thr Ala Asp Gly Asp Phe Pro Asp Thr Ile Gln Cys Ala Tyr Ile
                95                  100                 105

His Leu Val Ser Arg Glu Glu Cys Glu His Ala Tyr Pro Gly Gln
                110                 115                 120

Ile Thr Gln Asn Met Leu Cys Ala Gln Asp Glu Lys Tyr Gly Lys
                125                 130                 135

Asp Ser Cys Gln Gly Asp Ser Gly Gly
                140

<210> SEQ ID NO 2
<211> LENGTH: 148
<212> TYPE: PRT
<213> ORGANISM: Homo sapiens
<220> FEATURE:
<221> NAME/KEY: DOMAIN
<223> OTHER INFORMATION: Amino acid sequence of TADG-14 catalytic
      domain

<400> SEQUENCE: 2
```

```
Trp Val Val Thr Ala Ala His Cys Lys Lys Pro Lys Tyr Thr Val
1               5                   10                  15

Arg Leu Gly Asp His Ser Leu Gln Asn Lys Asp Gly Pro Glu Gln
                20                  25                  30

Glu Ile Pro Val Val Gln Ser Ile Pro His Pro Cys Tyr Asn Ser
                35                  40                  45

Ser Asp Val Glu Asp His Asn His Asp Leu Met Leu Leu Gln Leu
                50                  55                  60

Arg Asp Gln Ala Ser Leu Gly Ser Lys Val Lys Pro Ile Ser Leu
                65                  70                  75

Ala Asp His Cys Thr Gln Pro Gly Gln Asn Cys Thr Val Ser Gly
                80                  85                  90

Trp Gly Thr Val Thr Ser Pro Arg Glu Asn Phe Pro Asp Thr Leu
                95                  100                 105

Asn Cys Ala Glu Val Lys Ile Phe Pro Gln Lys Lys Cys Glu Asp
                110                 115                 120

Ala Tyr Pro Gly Gln Ile Thr Asp Gly Met Val Cys Ala Gly Ser
                125                 130                 135

Ser Lys Gly Ala Asp Thr Cys Gln Gly Asp Ser Gly Gly
                140                 145

<210> SEQ ID NO 3
<211> LENGTH: 146
<212> TYPE: PRT
<213> ORGANISM: unknown
<220> FEATURE:
<221> NAME/KEY: DOMAIN
<223> OTHER INFORMATION: Amino acid sequence of trypsin like serine
      protease (Try1) catalytic domain

<400> SEQUENCE: 3

Trp Val Val Ser Ala Gly His Cys Tyr Lys Ser Arg Ile Gln Val
1               5                   10                  15

Arg Leu Gly Glu His Asn Ile Glu Val Leu Glu Gly Asn Glu Gln
                20                  25                  30

Phe Ile Asn Ala Ala Lys Ile Ile Arg His Pro Gln Tyr Asp Arg
                35                  40                  45

Lys Thr Leu Asn Asn Asp Ile Met Leu Ile Lys Leu Ser Ser Arg
                50                  55                  60

Ala Val Ile Asn Ala Arg Val Ser Thr Ile Ser Leu Pro Thr Ala
                65                  70                  75

Pro Pro Ala Thr Gly Thr Lys Cys Leu Ile Ser Gly Trp Gly Asn
                80                  85                  90

Thr Ala Ser Ser Gly Ala Asp Tyr Pro Asp Glu Leu Gln Cys Leu
                95                  100                 105

Asp Ala Pro Val Leu Ser Gln Ala Lys Cys Glu Ala Ser Tyr Pro
                110                 115                 120

Gly Lys Ile Thr Ser Asn Met Phe Cys Val Gly Phe Leu Glu Gly
                125                 130                 135

Gly Lys Asp Ser Cys Gln Gly Asp Ser Gly Gly
                140                 145

<210> SEQ ID NO 4
<211> LENGTH: 144
<212> TYPE: PRT
<213> ORGANISM: unknown
<220> FEATURE:
<221> NAME/KEY: DOMAIN
<223> OTHER INFORMATION: Amino acid sequence of stratum corneum
```

-continued chymotryptic enzyme (scce) catalytic domain

<400> SEQUENCE: 4

Trp Val Leu Thr Ala Ala His Cys Lys Met Asn Glu Tyr Thr Val
1               5                   10                  15

His Leu Gly Ser Asp Thr Leu Gly Asp Arg Arg Ala Gln Arg Ile
            20                  25                  30

Lys Ala Ser Lys Ser Phe Arg His Pro Gly Tyr Ser Thr Gln Thr
            35                  40                  45

His Val Asn Asp Leu Met Leu Val Lys Leu Asn Ser Gln Ala Arg
        50                  55                  60

Leu Ser Ser Met Val Lys Lys Val Arg Leu Pro Ser Arg Cys Glu
65                  70                  75

Pro Pro Gly Thr Thr Cys Thr Val Ser Gly Trp Gly Thr Thr Thr
            80                  85                  90

Ser Pro Asp Val Thr Phe Pro Ser Asp Leu Met Cys Val Asp Val
            95                  100                 105

Lys Leu Ile Ser Pro Gln Asp Cys Thr Lys Val Tyr Lys Asp Leu
            110                 115                 120

Leu Glu Asn Ser Met Leu Cys Ala Gly Ile Pro Asp Ser Lys Lys
            125                 130                 135

Asn Ala Cys Asn Gly Asp Ser Gly Gly
            140

<210> SEQ ID NO 5
<211> LENGTH: 159
<212> TYPE: PRT
<213> ORGANISM: unknown
<220> FEATURE:
<221> NAME/KEY: DOMAIN
<223> OTHER INFORMATION: Amino acid sequence of hepsin (heps) catalytic
      domain

<400> SEQUENCE: 5

Trp Val Leu Thr Ala Ala His Cys Phe Pro Glu Arg Asn Arg Val
1               5                   10                  15

Leu Ser Arg Trp Arg Val Phe Ala Gly Ala Val Ala Gln Ala Ser
            20                  25                  30

Pro His Gly Leu Gln Leu Gly Val Gln Ala Val Val Tyr His Gly
            35                  40                  45

Gly Tyr Leu Pro Phe Arg Asp Pro Asn Ser Glu Glu Asn Ser Asn
            50                  55                  60

Asp Ile Ala Leu Val His Leu Ser Ser Pro Leu Pro Leu Thr Glu
65                  70                  75

Tyr Ile Gln Pro Val Cys Leu Pro Ala Ala Gly Gln Ala Leu Val
            80                  85                  90

Asp Gly Lys Ile Cys Thr Val Thr Gly Trp Gly Asn Thr Gln Tyr
            95                  100                 105

Tyr Gly Gln Gln Ala Gly Val Leu Gln Glu Ala Arg Val Pro Ile
            110                 115                 120

Ile Ser Asn Asp Val Cys Asn Gly Ala Asp Phe Tyr Gly Asn Gln
            125                 130                 135

Ile Lys Pro Lys Met Phe Cys Ala Gly Tyr Pro Glu Gly Gly Ile
            140                 145                 150

Asp Ala Cys Gln Gly Asp Ser Gly Gly
            155

<210> SEQ ID NO 6
<211> LENGTH: 1343
<212> TYPE: DNA
<213> ORGANISM: Homo sapiens
<220> FEATURE:
<223> OTHER INFORMATION: Nucleotide sequence encoding Tumor Antigen
      Derived Gene-14 (TADG-14) protein

<400> SEQUENCE: 6

```
ctgtagcagg cagagcttac caagtctctc cgaactcaaa tggaagaaat           50
accttatgaa tgtaagaatg taggggggtca tggcttgtaa tttacacagt          100
gtaaatgaaa ccatcctaga ggattatgag gaatcctttc tatgtgattt          150
tcaatcatag caagcaagaa aggctccagt gtcaaggtag ttcagctctt          200
acaggatata aaacagtcca tacttgagag aaaaaactta gatctgagtg          250
atggaatgtg aagcaaatct ttcaaaatca gtagacattt cttggacata          300
aaacacagat gaggaaaggg cttcaaatta gaagttacgt aatcaccatc          350
agaaagttca tgtttggtaa attctgttac tagaaatgta ggaaattcag          400
gtatagcttt gaatcccaat tacacattgg tcagtgggaa aactaagggc          450
ctccaacagg caaattcagg aggataggt ttcagggaat gccctggatt           500
ctggaagacc tcaccatggg acgccccga cctcgtgcgg ccaagacgtg           550
gatgttcctg ctcttgctgg ggggagcctg ggcaggacac tccagggcac          600
aggaggacaa ggtgctgggg ggtcatgagt gccaaccca ttcgcagcct           650 tggcaggcgg ccttgttcca gggccagcaa ctactctgtg gcggtgtcct          700
tgtaggtggc aactgggtcc ttacagctgc ccactgtaaa aaaccgaaat          750
acacagtacg cctgggagac cacagcctac agaataaaga tgcccagag           800 caagaaatac ctgtggttca gtccatccca caccctgct acaacagcag           850 cgatgtggag gaccacaacc atgatctgat gcttcttcaa ctgcgtgacc          900
aggcatccct ggggtccaaa gtgaagccca tcagcctggc agatcattgc          950
acccagcctg ccagaagtg caccgtctca ggctggggca ctgtcaccag          1000
tccccgagag aatttttcctg acactctcaa ctgtgcagaa gtaaaaatct         1050
ttccccagaa gaagtgtgag gatgcttacc cggggcagat cacagatggc         1100
atggtctgtg caggcagcag caaaggggct gacacgtgcc agggcgattc         1150
tggaggcccc ctggtgtgtg atggtgcact ccagggcatc acatcctggg         1200
gctcagaccc ctgtgggagg tccgacaaac ctggcgtcta taccaacatc         1250
tgccgctacc tggactggat caagaagatc ataggcagca agggctgatt         1300
ctaggataag cactagatct cccttaataa actcacggaa ttc                1343
```

<210> SEQ ID NO 7
<211> LENGTH: 260
<212> TYPE: PRT
<213> ORGANISM: Homo sapiens
<220> FEATURE:
<223> OTHER INFORMATION: Amino acid sequence of TADG-14 protein

<400> SEQUENCE: 7

```
Met Gly Arg Pro Arg Pro Arg Ala Ala Lys Thr Trp Met Phe Leu
1               5                   10                  15

Leu Leu Leu Gly Gly Ala Trp Ala Gly His Ser Arg Ala Gln Glu
                20                  25                  30
```

```
Asp Lys Val Leu Gly Gly His Glu Cys Gln Pro His Ser Gln Pro
         35                  40                  45

Trp Gln Ala Ala Leu Phe Gln Gly Gln Gln Leu Leu Cys Gly Gly
         50                  55                  60

Val Leu Val Gly Gly Asn Trp Val Leu Thr Ala Ala His Cys Lys
         65                  70                  75

Lys Pro Lys Tyr Thr Val Arg Leu Gly Asp His Ser Leu Gln Asn
         80                  85                  90

Lys Asp Gly Pro Glu Gln Glu Ile Pro Val Val Gln Ser Ile Pro
         95                 100                 105

His Pro Cys Tyr Asn Ser Ser Asp Val Glu Asp His Asn His Asp
        110                 115                 120

Leu Met Leu Leu Gln Leu Arg Asp Gln Ala Ser Leu Gly Ser Lys
        125                 130                 135

Val Lys Pro Ile Ser Leu Ala Asp His Cys Thr Gln Pro Gly Gln
        140                 145                 150

Lys Cys Thr Val Ser Gly Trp Gly Thr Val Thr Ser Pro Arg Glu
        155                 160                 165

Asn Phe Pro Asp Thr Leu Asn Cys Ala Glu Val Lys Ile Phe Pro
        170                 175                 180

Gln Lys Lys Cys Glu Asp Ala Tyr Pro Gly Gln Ile Thr Asp Gly
        185                 190                 195

Met Val Cys Ala Gly Ser Ser Lys Gly Ala Asp Thr Cys Gln Gly
        200                 205                 210

Asp Ser Gly Gly Pro Leu Val Cys Asp Gly Ala Leu Gln Gly Ile
        215                 220                 225

Thr Ser Trp Gly Ser Asp Pro Cys Gly Arg Ser Asp Lys Pro Gly
        230                 235                 240

Val Tyr Thr Asn Ile Cys Arg Tyr Leu Asp Trp Ile Lys Lys Ile
        245                 250                 255

Ile Gly Ser Lys Gly
        260
```

<210> SEQ ID NO 8
<211> LENGTH: 799
<212> TYPE: DNA
<213> ORGANISM: Mus musculus
<220> FEATURE:
<223> OTHER INFORMATION: Nucleotide sequence of mouse neuropsin
      homologous to TADG-14

<400> SEQUENCE: 8

```
agaggccacc atgggacgcc cccacccctg tgcaatccag ccgtggatcc         50
ttctgcttct gttcatggga gcgtgggcag ggctcaccag agctcagggc        100
tccaagatcc tggaaggtcg agagtgtata ccccactccc agccttggca        150
ggcagccttg ttccagggcg agagactgat ctgtggggt gtcctggttg         200 gagacagatg gtcctcacg gcagcccact gcaaaaaaca gaagtactcc         250
gtgcgtctgg gtgatcatag cctccagagc agagatcagc ggagcagga         300 gatccaggtg gctcagtcta tccagcatcc ttgctacaac aacagcaacc        350
cagaagatca cagtcacgat ataatgctca ttcgactgca gaactcagca        400
aacctcgggg acaaggtgaa gccggtccaa ctggccaatc tgtgtcccaa        450
agttggccag aagtgcatca tatcaggctg gggcactgtc accagccctc        500
aagagaactt tccaaacacc ctcaactgtg cggaagtgaa aatctattcc        550
```

```
cagaacaagt gtgagagagc ctatccaggg aagatcaccg agggcatggt        600
ctgtgctggc agcagcaatg gagctgacac gtgccagggt gactcaggag        650
gccctctggt gtgcgacggg atgctccagg gcatcacctc atggggctca        700 gaccoctgtg ggaaacccga gaaacctgga gtctacacca aaatctgccg        750
ctacactacc tggatcaaga agaccatgga caacagggac tgatcctgg         799
```

```
<210> SEQ ID NO 9
<211> LENGTH: 799
<212> TYPE: DNA
<213> ORGANISM: Homo sapiens
<220> FEATURE:
<223> OTHER INFORMATION: Nucleotide sequence of TADG-14 homologous to
      mouse neuropsin

<400> SEQUENCE: 9
agacctcacc atgggacgcc cccgacctcg tgcggccaag acgtggatgt        50
tcctgctctt gctgggggga gcctgggcag acactccag ggcacaggag         100 gacaaggtgc tggggggtca tgagtgccaa ccccattcgc agccttggca        150
ggcggccttg ttccagggcc agcaactact ctgtggcggt gtccttgtag        200
gtggcaactg ggtccttaca gctgcccact gtaaaaaacc gaaatacaca        250
gtacgcctgg gagaccacag cctacagaat aaagatggcc cagagcaaga        300
aatacctgtg gttcagtcca tcccacaccc ctgctacaac agcagcgatg        350
tggaggacca caaccatgat ctgatgcttc ttcaactgcg tgaccaggca        400
tccctggggt ccaaagtgaa gcccatcagc ctggcagatc attgcaccca        450
gcctggccag aagtgcaccg tctcaggctg ggcactgtc accagtcccc         500 gagagaattt tcctgacact ctcaactgtg cagaagtaaa aatctttccc        550
cagaagaagt gtgaggatgc ttacccgggg cagatcacag atggcatggt        600
ctgtgcaggc agcagcaaag gggctgacac gtgccagggc gattctggag        650 gcccctggt gtgtgatggt gcactccagg catcacatc ctggggctca         700 gaccoctgtg ggaggtccga caaacctggc gtctatacca acatctgccg        750
ctacctggac tggatcaaga agatcatagg cagcaagggc tgattctag         799
```

```
<210> SEQ ID NO 10
<211> LENGTH: 260
<212> TYPE: PRT
<213> ORGANISM: Mus musculus
<220> FEATURE:
<223> OTHER INFORMATION: Amino acid sequence of mouse neuropsin
      homologous to TADG-14

<400> SEQUENCE: 10

Met Gly Arg Pro Pro Cys Ala Ile Gln Pro Trp Ile Leu Leu
1               5                   10              15

Leu Leu Phe Met Gly Ala Trp Ala Gly Leu Thr Arg Ala Gln Gly
                20                  25                  30

Ser Lys Ile Leu Glu Gly Arg Glu Cys Ile Pro His Ser Gln Pro
                35                  40                  45

Trp Gln Ala Ala Leu Phe Gln Gly Glu Arg Leu Ile Cys Gly Gly
                50                  55                  60

Val Leu Val Gly Asp Arg Trp Val Leu Thr Ala Ala His Cys Lys
                65                  70                  75
```

-continued

```
Lys Gln Lys Tyr Ser Val Arg Leu Gly Asp His Ser Leu Gln Ser
            80              85                  90

Arg Asp Gln Pro Glu Gln Glu Ile Gln Val Ala Gln Ser Ile Gln
            95              100                 105

His Pro Cys Tyr Asn Asn Ser Asn Pro Glu Asp His Ser His Asp
            110             115                 120

Ile Met Leu Ile Arg Leu Gln Asn Ser Ala Asn Leu Gly Asp Lys
            125             130                 135

Val Lys Pro Val Gln Leu Ala Asn Leu Cys Pro Lys Val Gly Gln
            140             145                 150

Lys Cys Ile Ile Ser Gly Trp Gly Thr Val Thr Ser Pro Gln Glu
            155             160                 165

Asn Phe Pro Asn Thr Leu Asn Cys Ala Glu Val Lys Ile Tyr Ser
            170             175                 180

Gln Asn Lys Cys Glu Arg Ala Tyr Pro Gly Lys Ile Thr Glu Gly
            185             190                 195

Met Val Cys Ala Gly Ser Ser Asn Gly Ala Asp Thr Cys Gln Gly
            200             205                 210

Asp Ser Gly Gly Pro Leu Val Cys Asp Gly Met Leu Gln Gly Ile
            215             220                 225

Thr Ser Trp Gly Ser Asp Pro Cys Gly Lys Pro Glu Lys Pro Gly
            230             235                 240

Val Tyr Thr Lys Ile Cys Arg Tyr Thr Thr Trp Ile Lys Lys Thr
            245             250                 255

Met Asp Asn Arg Asp
            260
```